United States Patent [19]

Parker

[11] 4,229,467
[45] Oct. 21, 1980

[54] ALKOXY BENZOFURAN CARBOXYLIC ACIDS AND SALTS AND ESTERS THEREOF AS HYPOLIPIDEMIC AGENTS

[75] Inventor: Roger A. Parker, Cincinnati, Ohio

[73] Assignee: Richardson-Merrell Inc., Wilton, Conn.

[21] Appl. No.: 67,243

[22] Filed: Aug. 16, 1979

[51] Int. Cl.$^2$ .................. A61K 31/335; C07D 307/85
[52] U.S. Cl. ............................... 424/285; 260/346.22
[58] Field of Search .................. 260/346.22; 424/285

[56] References Cited

FOREIGN PATENT DOCUMENTS 1008260 10/1965 United Kingdom .

Primary Examiner—Henry R. Jiles
Assistant Examiner—Bernard Dentz
Attorney, Agent, or Firm—L. Ruth Hattan; Salvatore R. Conte

[57] ABSTRACT

Compounds of the Formula

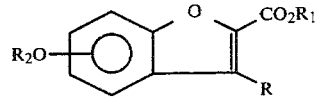

wherein R is H or $C_{1-4}$ alkyl; $R_1$ is H or $C_{1-4}$ alkyl; and $R_2$ is straight or branched chain alkyl of 10–20 carbon atoms, straight or branched chain alkenyl of 10–20 carbon atoms, straight or branched chain alkadienyl of 10–20 carbon atoms or straight or branched chain alkatrienyl of 10–20 carbon atoms and the pharmaceutically acceptable salts thereof, are useful as hypolipidemic agents.

10 Claims, No Drawings

ALKOXY BENZOFURAN CARBOXYLIC ACIDS AND SALTS AND ESTERS THEREOF AS HYPOLIPIDEMIC AGENTS

BACKGROUND OF THE INVENTION

This invention relates to alkoxy substituted benzofuran carboxylic acids, their esters and their pharmaceutically acceptable salts which are useful as hypolipidemic agents.

Saturated lower alkoxy substituted benzofuran carboxylic acids and esters are known. For example, such methoxy or ethoxy substituted acids are disclosed in U.S. Pat. Nos. 3,651,094, 3,751,430, 3,761,494 and 3,843,797 as well as Belgian Pat. No. 758,955 (French Pat. No. 2,073,349) and British Pat. Nos. 1,304,108 and 1,325,211. Such compounds containing alkoxy substituents having up to 6 or 7 carbon atoms are disclosed, e.g., in British Pat. No. 1,008,260 and U.S. Pat. No. 2,652,399. None of these compounds is disclosed as having hypolipidemic activity.

SUMMARY OF THE INVENTION

Compounds of Formula I:

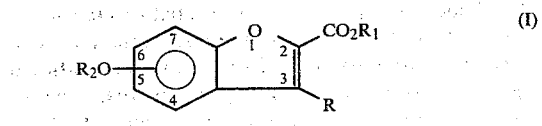

and their pharmaceutically acceptable salts, wherein R is H or $C_{1-4}$ alkyl; $R_1$ is H or $C_{1-4}$ alkyl; and $R_2$ is a straight or branched chain alkyl of 10–20 carbon atoms or a straight or branched chain alkenyl of 10–20 carbon atoms, are useful as hypolidemic agents.

DETAILED DESCRIPTION OF THE INVENTION

Illustrative examples of straight or branched lower alkyl chains which R and $R_1$ may represent as used herein are, for example methyl, ethyl, n-propyl, iso-propyl, n-butyl, iso-butyl, sec-butyl and tert-butyl.

Illustrative examples of straight or branched $C_{10-20}$ alkyl chains which $R_2$ may represent as used herein are, for example, decyl, undecyl, dodecyl, tridecyl, tetradecyl, pentadecyl, hexadecyl, heptadecyl, octadecyl, nonadecyl, eicosanyl, 3-methyl-heptadecyl, 3,7,11-trimethyl-dodecyl, 3,7-dimethyl-octadecyl, 3-methyl-tetradecyl, 3-ethyl-tetradecyl and the like.

Illustrative examples of straight or branched $C_{10-20}$ alkenyl chains include $C_{10-20}$ alkenyl, $C_{10-20}$ alkadienyl and $C_{10-20}$ alkatrienyl. Suitable such unsaturated groups include, for example, the aforementioned $C_{10-20}$ alkyl chains having 1-3 double bonds, e.g., decenyl, undecenyl, dodecenyl, etc., wherein the double bond may be in any position, such as heptadec-12-enyl, tridec-9-enyl, etc.; decdienyl, undecdienyl, dodecdienyl, tridecdienyl, etc., wherein the two individual double bonds may be in any combination of non-adjacent positions, preferably non-conjugated, such as 3,7-dimethyl-2,6-octadienyl, 2,7-hexadecadienyl, etc.; decatrienyl, undecatrienyl, dodecatrienyl, tridecatrienyl, etc., wherein the three individual double bonds may be in any combination of three positions, none of which are adjacent and preferably none of which are conjugated, such as 3,7,11-trimethyl-2,6,10-dodecatrienyl, 2,6,10-heptadecyltrienyl, etc.

For all $R_2$ groups, 12-16 carbon atoms are preferred. Particularly preferred are compounds wherein $R_2$ is tetradecyl and R is methyl and wherein $R_2O$ is in the 6-position. Preferred specific compounds are 6-tetradecyloxy-3-methyl-benzofuran-2-carboxylic acid and, especially, 6-tetradecyloxy-benzofuran-2-carboxylic acid.

The invention also includes the pharmaceutically acceptable salts of the compounds of Formula I wherein $R_1$ is hydrogen. Such salts include those formed with any suitable inorganic or organic bases such as those of alkali metals, for example, sodium and potassium; alkaline earth metals, for example, calcium and magnesium, light metals of Group IIIA, for example, aluminum; organic amines such as primary, secondary or tertiary amines, for example, cyclohexylamine, ethylamine and piperidine. These salts can be prepared by conventional means such as by contacting and neutralizing a solution of a compound of Formula I having a carboxylic acid group in a pure solvent with the stoichiometric quantity of a base, for example, sodium hydroxide.

Illustrative examples of compounds of this invention are, for example, 6-tetradecyloxybenzofuran-2-carboxylic acid; 3-methyl-6-(tetradecyloxy)-benzofuran-2-carboxylic acid; 6-tetradecyloxybenzofuran-2-carboxylic acid, methyl ester; 3-methyl-6-tetradecyloxybenzofuran-2-carboxylic acid, methyl ester; 6-(3,7,11-trimethyl-2,6,10-dodecatrienyloxy)-benzofuran-2-carboxylic acid; 6-(3,7-dimethyl-2,6-octadienyloxy)-benzofuran-2-carboxylic acid; 6-(3-methyl-6-tetradecyloxy)-benzofuran-2-carboxylic acid; 5-(3-ethyl-6-tetradecyloxy)-benzofuran-2-carboxylic acid; 5-(hexadecyloxy)-benzofuran-2-carboxylic acid; 5-(hexadecyloxy)-benzofuran-2-carboxylic acid, methyl ester; 4-(hexadecyloxy)-benzofuran-2-carboxylic acid; 6-(3,7-dimethyloctyl)-oxy-3-methyl-2-benzofuran carboxylic acid; and salts, preferably sodium or potassium salts, of the foregoing free acids.

The compounds of this invention are useful as hypolipidemic agents. They reduce blood lipids, particularly cholesterol and triglyceridies, without concurrent accumulation of desmosterol. These compounds can be administered to warm-blooded animals, mammals, rats, cats, dogs, pigs, cattle, horses, mice, sheep, poultry and humans and are useful in the treatment of hyperlipidemic states such as are encountered in patients with cardiovascular diseases that can result in heart failure and stroke. They are especially useful in treatment of artherosclerosis. As used herein, the term patient is intended to mean the animal or mammal being treated.

To illustrate the utility of the compounds of this invention, young male rats of the Wistar strain initially weighing about 175 g are given free access to a diet which contained 0.15% by weight of a compound of this invention. This diet is prepared by mixing the test compound with commercial Purina Chow. (Trademark of Ralston Purina, Co., St. Louis, Mo.). Groups of animals are given these diets for 4 days. Control groups of 6 rats each are given Purina Chow to which no test compound has been added. At the end of the treatment period all rats are bled by cardiac puncture, and the plasma is analyzed for cholesterol and triglyceride content. The results of such testing of two compounds of this invention are given in the following Table 1.

TABLE 1

| Test Compound: | 6-tetradecyloxy-benzofuran-2-carboxylic acid | 6-tetradecyloxy-3-3-methyl-benzofuran-2-carboxylic acid |
| --- | --- | --- |
| Duration of treatment (Days): | 4 | 4 |
| Daily Dose mg/kg (a): | 167 | 138 |
| No. Rats: | 6 | 6 |
| Plasma Cholesterol % Reduction (b): | 34 | 20 |
| Plasma Triglycerides % Reduction (b): | 61 | 64 |

(a) Determined by measuring food consumption.
(b) Compared to untreated control rats in the same experiment.

The compounds of this invention can be administered orally or parenterally either alone or in the form of a pharmaceutical preparation. Pharmaceutical preparations containing conventional pharmaceutical carriers and as active ingredients compounds of this invention can be employed in unit dosage forms such as solids, for example, tablets, capsules, and pills, or liquid solutions, suspensions, or emulsions for oral and parenteral administration. The dosage unit administered can be any lipid lowering effective amount. The quantity of compound administered can vary over a wide range to provide from about 0.5 mg/kg (milligram per kilogram) to about 200 mg/kg of body weight of the patient per day, and preferably from about 10 mg/kg to 30 mg/kg of body weight of the patient per day, to achieve the desired effect. Unit doses can contain from about 50 mg to 1 g of a compound of this invention and may be administered, for example, from 1 to 4 times daily.

The compounds of this invention may be prepared by a conventional Perkin or Claisen condensation using a starting material substituted coumarin of the following Formula II:

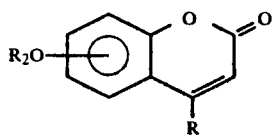

(II)

wherein R and R$_2$ are as defined above.

The substituted coumarin of Formula II is first brominated by reaction with an equivalent or slightly excess amount of bromine. The reaction is generally carried out in the presence of a solvent such as a chlorinated hydrocarbon, e.g., methylene chloride, chloroform, ethylene chloride or carbon tetrachloride. The reaction time may vary from about 15 minutes to about 24 hours, depending upon the reactants, the solvent and the reaction temperature which may vary from about 0° C. up to about the reflux temperature of the solvent.

The dibromo intermediate produced by the bromination step is subsequently subjected to basic hydrolysis, e.g., using an alcoholic alkali metal hydroxide, e.g., NaOH or KOH, in methanol, ethanol, isopropanol or n-propanol. The hydrolysis may be carried out at a wide range of temperatures, e.g., from about 0° C. up to about the reflux temperature of the alcoholic solvent, generally, for a period of time of from about 15 minutes up to about 24 hours. This hydrolysis may be preceded by treatment with aqueous Na$_2$SO$_3$ or a similar agent.

The reaction may be summarized as follows:

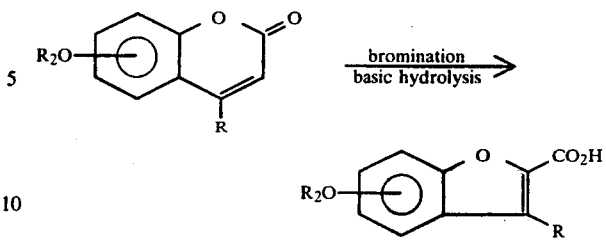

Such a Perkin condensation may also be employed when the R$_2$ side chain is unsaturated. However, in this case, bromination of the side chain will occur, necessitating an additional step for debromination. Such a debromination reaction can be carried out under fully conventional conditions well known to those of ordinary skill in the art.

The starting material alkoxy coumarins may be prepared by alkylating the corresponding 5-, 6-, 7- or 8-hydroxy coumarin using an R$_2$-halide under basic conditions. For example, an alkali metal hydroxide, e.g., NaOH or KOH, or an alkali metal salt, e.g., NaOCH$_3$, NaOC$_2$H$_5$, K$_2$CO$_3$, etc. may be employed as the base. The halide reactant may be saturated or unsaturated as required by the finally desired structure. The reaction time may vary from about 2 to 12 hours depending upon the reactants, the solvent if any and the reaction temperature, which may vary from about room temperature to about the reflux temperature of the solvent. The hydroxy coumarins are known compounds, as are the R$_2$-halides which can readily be prepared from the corresponding R$_2$-alcohols.

The compounds of this invention can also be prepared from the readily available 2,3-, 2,4-, 2,5- or 2,6-dihydroxy-benzaldehydes, as follows:

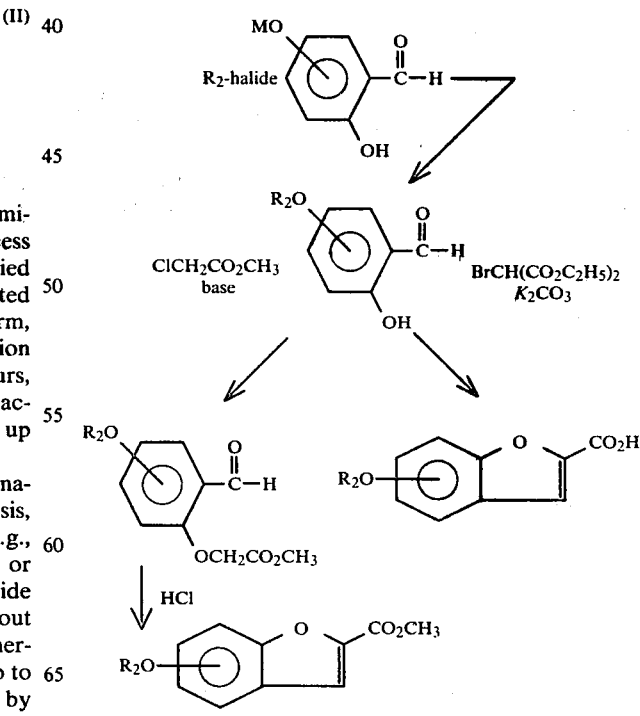

wherein M is an alkali metal, e.g., Na or K.

The $R_2$-halide, e.g., a bromide, may be reacted with the metaloxy-substituted ortho-hydroxybenzaldehyde under fully conventional conditions to form the corresponding alkoxy substituted compound. The illustrated 2-step condensation may be conducted by reacting the ortho-hydroxybenzaldehyde with a lower-alkyl haloacetate, such as the methyl-chloroacetate shown, under basic conditions, e.g., in the presence of an alkali metal base or salt, such as NaOH or sodium ethoxide, sodium methoxide, etc. The reaction may be conducted with or without a solvent. Suitable solvents for this reaction, if desired, are non-protic solvents such as ethereal solvents, e.g., diethyl ether, tetrahydrofuran and the like; dimethylformamide and dimethylsulfoxide. The reaction may be carried out over a wide range of temperatures which may vary from about room temperature to about the reflux temperature of the solvent. The reaction time may vary from about 2 hours to about 12 hours, depending upon the reactants, the solvent, if any, and the reaction temperature. The second step of the condensation is generally carried out under acid catalyzed conditions, e.g., using a strong acid such as HCl. The reaction may be carried out with or without a solvent. When a solvent is employed, alcoholic solvents may be used, e.g., methanol, ethanol, isopropanol, n-propanol, n-butanol and the like. The reaction time may vary from about 2 to about 12 hours, depending upon the reactants, the solvent, if any, and the reaction temperature which may vary from about room temperature to about the reflux temperature of the solvent.

The illustrated 1-step condensation may be carried out by reacting the ortho-hydroxybenzaldehyde with a lower-alkyl halomalonate, such as the ethyl bromomalonate shown. The reaction is carried out under basic conditions, e.g., with the addition of an alkali metal hydroxide, e.g., KOH or NaOH, or an alkali metal salt such as $NaOC_2H_5$, $NaOCH_3$, $K_2CO_3$ and the like. The reaction may be carried out with or without a solvent. When a solvent is employed, non-protic solvents such as those mentioned above can be used. The reaction time may vary from about 2 to about 12 hours, depending upon the reactants, the solvent, if any, and the reaction temperature which may vary from about room temperature to about the reflux temperature of the solvent.

The starting material ortho-hydroxybenzaldehydes can be prepared using fully conventional methods known to those of ordinary skill in the art from the commercially available 2,3-; 2,4-; 2,5-; and 2,6-dihydroxybenzoic acids.

Other general methods for preparing alkoxy-benzofuran-2-carboxylic acids and esters thereof are also known. For example, see the Chemistry of Heterocyclic Compounds, Vol. 29, "The Benzofurans," A. Mustafa, John Wiley and Sons (New York 1974), Chapter III, pp. 111-114; or Principles of Modern Heterocyclic Chemistry, L. A. Paquette, W. A. Benjamin, Inc. (New York, 1968), pp. 160-162.

The esters of the carboxylic acids prepared by the foregoing methods may be prepared by fully conventional methods well known to those of ordinary skill in the art. For example, the esters may be prepared by reaction of the desired acid with the corresponding $R_1$-halide under basic conditions. For example, the reaction may be conducted in the presence of a base such as $K_2CO_3$, $NaOCH_3$, $NaOC_2H_5$, etc. The reaction is normally conducted for a period of time of about 15 minutes to about 10 hours at a temperature of about 0° C. to about the reflux temperature of the halide.

The following specific examples are illustrative of the invention.

EXAMPLE 1

Preparation of Starting Material:
7-Tetradecyloxy-coumarin 16.2 g (0.100 mole) of 7-hydroxy-coumarin, 5.4 g (0.100 mole) of sodium methoxide and 300.0 ml of dry dimethylformamide are stirred at room temperature for ½ hour. 27.7 g (0.100 mole) of 1-bromotetradecane is added and the mixture is stirred at room temperature for 15 minutes. It is then heated overnight on a steam bath under reduced pressure to remove the methanol formed. The solvent is removed under further reduced pressure and the mixture is extracted with ether/$H_2O$. The ether layer is washed with 5% NaOH, $H_2O$ and saline solution. It is dried ($Na_2SO_4$) and distilled-off. After being added to about 200 ml of hexane, it is cooled in an ice bath. 19.2 g (57%) of product is obtained. After recrystallization from methanol, a white solid of 7-tetradecyloxy-coumarin is obtained, m.p. 59°-60° C.

EXAMPLE 2

Preparation of Starting Material:
7-Tetradecyloxy-4-methyl-coumarin 35.2 g (0.2 mole) of 7-hydroxy-4-methyl-coumarin, 27.6 g (0.2 mole) of potassium carbonate, 55.4 g (0.2 mole) of 1-bromotetradecane and 600.0 ml of dry dimethylformamide are stirred in a steam bath overnight. The mixture is cooled and extracted into 1.5 liters of diethyl ether. The ether layer is washed 5 times with saturated saline. It is dried ($Na_2SO_4$) and evaporated. The ether is replaced with 800 ml of hexane. The mixture is recrystallized therefrom, yielding 68.3g (92%) of 7-tetradecyloxy-4-methyl-coumarin, m.p. 61°-62° C.

EXAMPLE 3

6-Tetradecyloxy-benzofuran-2-carboxylic acid 5.0 g (0.0148 mole) of 7-tetradecyloxy-coumarin and 100 ml of dry methylene chloride are cooled in an ice bath. 2.37 g (0.0148 mole) of bromine and 50.0 ml of dry methylene chloride are added over ½ hour. The mixture is stirred at room temperature for 1.5 hours. It is then diluted with 20 ml of 10% $Na_2SO_3$, and the methylene chloride layer is separated, dried ($Na_2SO_4$) and evaporated to dryness. The white solid obtained is combined with 100 ml of ethanolic KOH (30 g KOH/100 ml ethanol). The mixture is heated to reflux, diluted with 300 ml of ethanol and the reflux continued for 2 hours. It is then allowed to stand at room temperature overnight. The mixture is acidified with concentrated HCl and extracted into ether. The ether layer is washed, dried ($Na_2SO_4$) and evaporated to dryness to yield about 5 g of 6-tetradecycloxy-benzofuran-2-carboxylic acid.

EXAMPLE 4

6-Tetradecyloxy-benzofuran-2-carboxylic acid 5.0 g (0.0148 mole) of 7-tetradecyloxy-coumarin and 100.0 ml of carbon tetrachloride are stirred at room temperature. 2.37 g (0.0148 mole) of bromine and 50.0 ml of carbon tetrachloride are added over a ½ hour period. The mixture is stirred at room temperature for 2 hours. 30 ml of 10% $Na_2SO_3$ is added. The carbon tetrachloride layer is separated, dried ($Na_2SO_4$) and evaporated to dryness. The product obtained is added to 75 ml of ethanol (containing 32 g of KOH) at room temperature. The mixture is stirred and heated to reflux. It is then diluted in 300 ml of ethanol and refluxed overnight. It is allowed to cool and is acidified with HCl. After extraction into ether, the ether layer is washed (H$_2$O), dried (Na$_2$SO$_4$) and evaporated to dryness.

The product obtained is combined with the product obtained from EXAMPLE 3 in ether and the mixture crystallized from hexane/ether to yield 6.4 g of 6-tetradecyloxy-benzofuran-2-carboxylic acid as a white solid. m.p. 131°–135° C.

EXAMPLE 5

3-Methyl-6-tetradecyloxy-benzofuran-2-carboxylic acid 10.9 g (0.0292 mole) of 7-tetradecyloxy-4-methyl-coumarin and 250 ml of dry methylene chloride is stirred at room temperature. 4.68 g (0.0292 mole) of bromide and 100.0 ml of dry methylene chloride are added over a period of 20 minutes. The mixture is stirred at room temperature for 1 hour and refluxed for 15 minutes. The mixture is then cooled and extracted with 10% Na$_2$SO$_3$. It is washed with a saline solution, dried (Na$_2$SO$_4$) and evaporated to dryness. The product obtained is stirred into a cold solution of 60 g KOH and 150 ml of ethanol. The mixture is heated to reflux for 2 hours and then is diluted with water. After refluxing is continued for about 10 minutes, it is poured into 1 liter of water, acidified with concentrated HCl and extracted with diethyl ether. The ether layer is washed with water and saline solution, dried (Na$_2$SO$_4$) and evaporated with replacement of the solvent with a total volume of 150 ml of hexane. The mixture is allowed to stand at room temperature. The product is collected and dried, yielding 10.4 g (92%) of 3-methyl-6-tetradecyloxybenzofuran-2-carboxylic acid, m.p. 108°–110° C. The mother liquor is concentrated to about 50 ml and cooled, yielding an additional 0.4 g of the 3-methyl-6-tetradecyloxy-benzofuran-2-carboxylic acid, m.p. 105°–108° C. (Overall yield — 96%.)

EXAMPLE 6

3-Methyl-6-tetradecyloxy-benzofuran-2-carboxylic acid, methyl ester 0.4 g (1.03 mmoles) of 3-methyl-6-tetradecyloxy-benzofuran-2-carboxylic acid and 0.3 g (2.00 mmoles) of 1-methyl-3-p-tolyltriazine are stirred in ether and refluxed for 15 minutes. The mixture is then allowed to stand at room temperature for 1 hour. It is then refluxed for 15 minutes. The reaction mixture is worked-up by extraction with diethyl ether and HCl. The ether is distilled off and is replaced by dioxane. The resultant mixture is heated on a steam bath for 1 hour. It is then extracted with diethyl ether/HCl, H$_2$O and NaHCO$_3$ (aq.). The extract is evaporated and the ether replaced with methanol. The methyl ester of 3-methyl-6-tetradecyloxy-benzofuran-2-carboxylic acid is allowed to crystallize from the mixture.

EXAMPLE 7

6-(3,7-Dimethyloctyl)-oxy-3-methyl-benzofuran-2-carboxylic acid 18.0 g (0.057 mole) of 3,7-dimethyloctyloxy-4-methyl-coumarin and 400 ml of dried methylene chloride are stirred at room temperature. 9.6 g (0.06 mole) of bromine and 100 ml of methylene chloride is added over 10 minutes. The solvent is distilled off under reduced pressure to give a low melting solid. This is combined with 50 g of potassium hydroxide in 150 ml of anhydrous ethanol at room temperature. The reaction mixture is heated to reflux with stirring for 1 hour. It is then diluted with 150 ml of water and the refluxing continued for another 15 minutes. The reaction is cooled and diluted to a volume of 2 liters with water. It is acidified with concentrated hydrochloric acid. The precipitate is collected and dried, yielding 18.8 g of a tan solid which is recrystallized from ether/hexane, yielding 14.8 g of 6-(3,7-dimethyloctyl)-oxy-3-methyl-benzofuran-2-carboxylic acid, m.p. 107°–108° C.

EXAMPLES 8–13

Using the procedures of any of Examples 3–5, when a substituted coumarin listed below is substituted for the coumarin employed in the corresponding example, the respective products listed in the table below are obtained.

TABLE 2

| Example Number | Substituted Coumarin | Product |
|---|---|---|
| 8 | 7-(3,7,11-trimethyl-2,6,10-dodecatrienyloxy)-coumarin | 6-(3,7,11-trimethyl-2,6,10-dodecatrienyl-oxy)-benzofuran-2-carboxylic acid |
| 9 | 7-(3,7-dimethyl-2,6-octa-dienyloxy)-coumarin | 6-(3,7-dimethyl-2,6-octadienyloxy)-benzofuran-2-carboxylic acid |
| 10 | 7-(3-methyl-6-tetra-decyl-oxy)-coumarin | 6-(3-methyl-6-tetradecyloxy)-benzofuran-2-carboxylic acid |
| 11 | 6-(3-ethyl-6-tetra-decyl-oxy)-coumarin | 5-(3-ethyl-6-tetra-decyloxy)-benzofuran-2-carboxylic acid |
| 12 | 6-(hexadecyloxy)-coumarin | 5-(hexadecyloxy)-benzofuran-2-carboxylic acid |
| 13 | 5-(hexadecyloxy)-coumarin | 4-(hexadecyloxy)-benzofuran-2-carboxylic acid |

EXAMPLES 14 and 15

When in the procedure of EXAMPLE 6, 5-(hexadecyloxy)-benzofuran-2-carboxylic acid (EXAMPLE 14) or 6-(tetradecyloxy)-benzofuran-2-carboxylic acid (EXAMPLE 15) is substituted for the starting material benzofuran-2-carboxylic acid utilized in EXAMPLE 6, the respective product is 5-(hexadecyloxy)-benzofuran-2-carboxylic acid, methyl ester or 6-(tetradecyloxy)-benzofuran-2-carboxylic acid, methyl ester.

EXAMPLE 16

An illustrative composition for tablets is as follows:

|  | Per Tablet |
|---|---|
| (a) 4-tetradecyloxy-benzofuran-2-carboxylic acid | 100.0 mg |
| (b) wheat starch | 15.0 mg |
| (c) lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 17

An illustrative composition for a parenteral injection is the following wherein the quantities are on a weight to volume basis.

|  | Amount |
|---|---|
| (a) 6-tetradecyloxy-benzofuran-2-carboxylic acid, sodium salt | 100.0 mg |
| (b) sodium chloride | q.s. |
| (c) water for injection to make | 20 ml |

The composition is prepared by dissolving the active ingredient (a) and sufficient sodium chloride in water for injection to render the solution isotonic. The composition may be dispensed in a single ampoule containing 100 mg of the active ingredient for multiple dosage or in 20 ampoules for single dosage.

EXAMPLE 18

An illustrative composition for hard gelatin capsules is as follows:

|  | Amount |
|---|---|
| (a) 6-tetradecyloxy-benzofuran-2-carboxylic acid | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 19

An illustrative composition for pills is the following:

|  | Per Pill |
|---|---|
| (a) 6-tetradecyloxy-benzofuran-2-carboxylic acid | 200 mg |
| (b) corn starch | 130 mg |
| (c) liquid glucose | 20 ml |

The pills are prepared by blending the active ingredient (a) and the corn starch then adding the liquid glucose with thorough kneading to form a plastic mass from which the pills are cut and formed.

I claim:

1. A compound of the formula

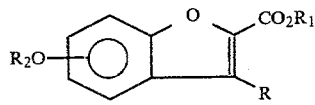

wherein R is H or $C_{1-4}$ alkyl; $R_1$ is H or $C_{1-4}$ alkyl; and $R_2$ is straight or branched chain alkyl of 10–20 carbon atoms, straight or branched chain alkenyl of 10–20 carbon atoms, straight or branched chain alkadienyl of 10–20 carbon atoms or straight or branched chain alkatrienyl of 10–20 carbon atoms, and the pharmaceutically acceptable salts thereof.

2. A compound of claim 1, wherein $R_2$ is of 12–16 carbon atoms.

3. A compound of claim 2, wherein $R_2$ is tetradecyl.

4. A compound of claim 1, wherein $R_1$ is H.

5. A compound of claim 1, wherein R is H or methyl.

6. A compound of claim 1, wherein $R_2O$ is at the 6-position.

7. 6-Tetradecyloxy-benzofuran-2-carboxylic acid, a compound of claim 1.

8. 6-Tetradecyloxy-3-methyl-benzofuran-2-carboxylic acid, a compound of claim 1.

9. A pharmaceutical composition comprising in unit dosage form from about 50 mg to 1 g of a compound of claim 1 and a significant amount of a pharmaceutically acceptable carrier.

10. A method of lowering serum lipids in a mammal which comprises administering thereto an amount of a compound of claim 1 effective to lower significantly the serum lipids thereof.

* * * * *